(12) United States Patent
Kotov et al.

(10) Patent No.: US 8,080,183 B2
(45) Date of Patent: Dec. 20, 2011

(54) NANOPARTICLE ASSEMBLIES WITH MOLECULAR SPRINGS

(75) Inventors: Nicholas Kotov, Ypsilanti, MI (US); Joebeom Lee, Ann Arbor, MI (US); Alexander Govorov, Athens, OH (US)

(73) Assignee: Ohio University, Athens, OH (US)

( * ) Notice: Subject to any disclaimer, the term of this patent is extended or adjusted under 35 U.S.C. 154(b) by 480 days.

(21) Appl. No.: 11/915,591

(22) PCT Filed: May 30, 2006

(86) PCT No.: PCT/US2006/020937
§ 371 (c)(1),
(2), (4) Date: Nov. 18, 2008

(87) PCT Pub. No.: WO2006/128181
PCT Pub. Date: Nov. 30, 2006

(65) Prior Publication Data
US 2009/0117002 A1    May 7, 2009

Related U.S. Application Data

(60) Provisional application No. 60/685,741, filed on May 27, 2005.

(51) Int. Cl.
*H01B 1/02* (2006.01)
*H01B 1/04* (2006.01)
*H01B 1/06* (2006.01)

(52) U.S. Cl. .............. 252/519.4; 252/512; 252/519.5; 977/724; 977/810; 977/813

(58) Field of Classification Search .......... 252/512, 252/519.4, 519.5; 422/55; 977/700, 724, 977/731, 762, 773, 774, 810, 813
See application file for complete search history.

(56) References Cited

OTHER PUBLICATIONS

R. C. Mucic et al., DNA-Directed Synthesis of Binary Nanoparticle Network Materials, 120 J. Am. Chem. Soc. 12674-12675 (1998).*
B. Mergell et al., Modeling DNA Structure, Elasticity, and Deformations at the Base-Pair Level, 68 Phys. Rev. E 021911-1-021911-15 (2003).*
Z. Gueroui and A. Libchaber, Single-Molecule Measurements of Gold-Quenched Quantum Dots, 93 Phys. Rev. Lett. 166108-1-166108-4 (2004).*
R. Baron et al., Hydrogen-Bonded CdS Nanoparticle Assemblies on Electrodes for Photochemical Applications, 44 Angew. Chem. Int. Ed. 4010-4015 (2005).*
E. Oh et al., Inhibition Assay of Biomolecules Based on Fluorescence Resonance Energy Transfer (FRET) Between Quantum Dots and Gold Nanoparticles, 127 J. Am. Chem. Soc. 3270-3271 (2005).*
K. K. Vamsi et al., Interaction of Surface Plasmons with CdTe Quantum Dot Excitons, 5955 Proc. SPIE 59550L-1-59550L-6 (2005).*
M. Hamdi et al., Molecular Nanosprings for Protein-Based Nanorobotics, Proceedings of the 2006 IARP—IEEE/RAS—EURON Joint Workshop on: Micro & Nano Robotics, Paris, France, Oct. 23-24, 2006.*
H.-R. Jiang and M. Sano, Stretching Single Molecular DNA by Temperature Gradient, 91 Appl. Phys. Lett. 154104 (2007).*

(Continued)

*Primary Examiner* — Walter D. Griffin
*Assistant Examiner* — Randy Boyer
(74) *Attorney, Agent, or Firm* — Jason H. Foster; Kremblas & Foster

(57) ABSTRACT

A nanoscale sensing device from different types of nanoparticles (NPs) and nanowires (NWs) connected by molecular springs. The distance between the nanoscale colloids reversibly changes depending on conditions or analyte concentration and can be evaluated by fluorescence measurements.

19 Claims, 2 Drawing Sheets

OTHER PUBLICATIONS

S. Fujii et al., Observation of DNA Pinning at Laser Focal Point on Au Surface and its Application to Single DNA Nanowire and Cross-Wire Formation, 80 Bioelectrochem. 26-30 (2010).*

Atwater, Harry A. et al. The New "p-n Junction": Plasmonics Enables Photonic Access to the Nanoworld. Mrs. Bulletin, vol. 30, May 2005, pp. 385-389.

Bernas, Tytus et al. Loss of Image Quality in Photobleaching During Microscopic Imaging of Fluorescent Probes Bound to Chromatin. Journal of Biomedical Optics, vol. 10(6), Nov./Dec. 2005, pp. 064015-1-064015-9.

Bjork, Lars et al. Computerized Assessment of Production of Multiple Human Cytokines at the Single-Cell Level Using Image Analysis. Journal of Leukocyte Biology, vol. 59, Feb. 1996, pp. 287-295.

Chapman, Andrew P. PEGylated Antibodies and Antibody Fragments for Improved Therapy: A Review. Advanced Drug Delivery Reviews 54 (2002), pp. 531-545.

Chen, Shihong et al. Amperometric Hydrogen Peroxide Biosensor Based on the Immobilization of Horseradish Peroxidase (HRP) on the Layer-by-Layer Assembly Films of Gold Colloidal Nanoparticles and Toluidine Blue. Electroanalysis vol. 18, No. 5, 2006, pp. 471-477.

Citrin, D.S. Coherent Excitation Transport in Metal-Nanoparticle Chains. Nano Letters, vol. 4, No. 9, Sep. 2004, pp. 1561-1565.

Dulkeith, E. et al. Fluorescence Quenching of Dye Molecules near Gold Nanoparticles: Radiative and Nonradiative Effects. Physical Review Letters, vol. 89, No. 20, Nov. 11, 2002, pp. 203002-1-203002-4.

Dyadyusha, H. et al. Quenching of CdSe Quantum Dot Emission, a New approach for Biosensing. Chem. Commun., 2005, pp. 3201-3203.

Fu, Aihua et al. Discrete Nanostructures of Quantum Dots/AU with DNA. J. Am. Chem. Soc., 126, 2004, pp. 10832-10833.

Gomez-Mouton, Concepcion et al. Dynamic Redistribution of Raft Domains as an Organizing Platform for Signaling During Cell Chemotaxis. The Journal of Cell Biology, vol. 164, No. 5, Mar. 1, 2004, pp. 759-768.

Goucher, D. R. et al. A Quantitative Determination of Multi-Protein Interactions by the Analysis of Confocal Images Using a Pixel-by-Pixel Assessment Algorithm. Bioinformatics Original Paper, vol. 21, No. 15, 2005, pp. 3248-3254.

Govorov, Alexander O. et al. Exciton-Plasmon Interaction and Hybrid Excitons in Semiconductor-Metal Nanoparticle Assemblies. Nano Letters, vol. 6, No. 5, 2006, pp. 984-994.

Gueroui, Zoher et al. Single-Molecule Measurements of Gold-Quenched Quantum Dots. Physical Review Letters, vol. 93, No. 16, Oct. 15, 2004, pp. 166108-1-166108-4.

Heller, Daniel A. et al. Optical Detection of DNA Conformational Polymorphism on Single-Walled Carbon Nanotubes. Science, vol. 311, Jan. 27, 2006, pp. 508-511.

Ipe, Binil Itty et al. Investigations on Nanoparticle-Chromophore and Interchromophore Interactions in Pyrene-Capped Gold Nanoparticles. J. Phys. Chem. B 2004, 108, pp. 13265-13272.

Jana, Nikhil R. et al. Seeding Growth for Size Control of 5-40 nm Diameter Gold Nanoparticles. Langmuir, 2001, 17, pp. 6782-6786.

Kang, Youngjong et al. Plasmonic Nanoparticle Chains via a Morphological, Sphere-to-String Transition. J. Am. Chem. Soc. 2005, 127, pp. 13800-13801.

Lakowicz, Joseph R. et al. Advances in Surface-Enhanced Fluorescence. Journal of Fluorescence, vol. 14, No. 4, Jul. 2004, pp. 425-441.

Lee, Jaebeom et al. Bioconjugates of CdTe Nanowires and Au Nanoparticles: Plasmon-Exciton Interactions, Luminescence Enhancement, and Collective Effects. Nano Letters, vol. 4, No. 12, 2004, pp. 2323-2330.

Lee, Jaebeom et al. Bioconjugated Superstructures of CdTe Nanowires and Nanoparticles: Multistep Cascade Forster Resonance Energy Transfer and Energy Channeling. Nano Letters, vol. 5, No. 10, 2005, pp. 2063-2069.

Lee, Jaebeom et al. Nanoparticle Assemblies with Molecular Springs: A Nanoscale Thermometer. Angew. Chem. Int. Ed., 2005, 44, 7439-7442.

Levin, Carly S. et al. Chain-Length-Dependent Vibrational Resonances in Alkanethiol Self-Assembled Monolayers Observed on Plasmonic Nanoparticle Substrates. Nano Letters, vol. 6, No. 11, 2006, pp. 2617-2621.

Liz-Marzan, Luis. Tailoring Surface Plasmons through the Morphology and Assembly of Metal Nanoparticles. Langmuir, vol. 22, No. 1, 2006, pp. 32-41.

Maier, Stefan A. et al. Local Detection of Electromagnetic Energy Transport Below the Diffraction Limit in Metal Nanoparticle Plasmon Waveguides. Nature Materials, vol. 2, Apr. 2003, pp. 229-232.

Maye, Mathew M. et al. A Simple Method for Kinetic Control of DNA-Induced Nanoparticle Assembly. J. Am. Chem. Soc., 2006, 128, pp. 14020-14021.

Miyake, Masao et al. Electrical Properties of CdTe Layers Electrodeposited from Ammoniacal Basic Electrolytes. Journal of the Electrochemical Society, 150 (6), 2003, pp. C413-C419.

Nagayoshi, Hiroshi et al. Growth of Thick CdTe Films by Close-Space-Sublimation Technique. Nuclear Science Symposium Conference Record 7, (2004) pp. 4411-4414.

Niemeyer, Christof M. Functional Hybrid Devices of Proteins and Inorganic Nanoparticles. Angew. Chem. Int. Ed. 2003, 42, pp. 5796-5800.

Nikoobakht, Babak et al. The Quenching of CdSe Quantum Dots Photoluminescence by Gold Nanoparticles in Solution. Photochemistry and Photobiology, 2002, 75(6), pp. 591-597.

Obare, Sherine O. et al. Sensing Strategy for Lithium Ion Based on Gold Nanoparticles. Langmuir 2002, 18, pp. 10407-10410.

Oh, Eunkeu et al. Inhibition Assay of Biomolecules Based on Fluorescence Resonance Energy Transfer (FRET) between Quantum Dots and Gold Nanoparticles. J. Am. Chem. Soc., 2005, 127, pp. 3270-3271.

Prouty, Angela M. et al. Multiphoton Laser Scanning Microscopy as a Tool for *Xenopus* Oocyte Research. Methods in Molecular Biology, vol. 322:*Xenopus* Protocols: Cell Biology and Signal Transduction, pp. 87-101, (2006).

Sarathy, K. Vijaya et al. Superlattices of Metal and Metal-Semiconductor Quantum Dots Obtained by Layer-by-Layer Deposition of Nanoparticle Arrays. J. Phys. Chem. B 1999, 103, pp. 399-401.

Stauffer, Jimmy K. et al. Multicolor Fluorescence-Based Approaches for Imaging Cytokine-Induced Alterations in the Neovascularization, Growth, Metastasis, and Apoptosis of Murine Neuroblastoma Tumors. J Immunother, vol. 29, No. 2, Mar./Apr. 2006, pp. 151-164.

Tang, Zhiyong et al. One-Dimensional Assemblies of Nanoparticles: Preparation, Properties, and Promise. Adv. Mater., Apr. 18, 2005, 17, No. 8, pp. 951-962.

Turkevych, I. et al. High-Temperature Electron and Hole Mobility in CdTe. Semicond. Sci. Technol. 17, 2002, pp. 1064-1066.

Wallrabe, Horst et al. Issues in Confocal Microscopy for Quantitative FRET Analysis. Microscopy Research and Technique 69, 2006, pp. 196-206.

Wang, Gangli et al. Controlled Assembly of Monolayer-Protected Gold Clusters by Dissolved DNA. Nano Letters vol. 4, No. 1, 2004, pp. 95-101.

Wei, Q.-H. et al. Plasmon Resonance of Finite One-Dimensional Au Nanoparticle Chains. Nano Letters, vol. 4, No. 6, 2004, pp. 1067-1071.

Westenhoff, Sebastian et al. Quantum Dot on a Rope. J. Am. Chem. Soc., vol. 124, No. 11, 2002, pp. 2448-2449.

Yamamoto, Yoko et al. Site-Specific PEGylation of a Lysine-Deficient TNF-a with Full Bioactivity. Nature Biotechnology, vol. 21, May 2003, pp. 546-552.

Zhang, Haifei et al. Aligned Two-and Three Dimensional Structures by Directional Freezing of Polymers and Nanoparticles. Nature Materials, vol. 4, Oct. 2005, pp. 787-793.

Zhang, Jiguang et al. A New Approach to Hybrid Polymer-Metal and Polymer-Semiconductor Particles. Adv. Mater. Dec. 3, 2002, 14, No. 23, pp. 1756-1759.

Zhu, Tao et al. Surface Modification of Citrate-Reduced Colloidal Gold Nanoparticles with 2-Mercaptosuccinic Acid. Langmuir 2003, 19, pp. 9518-9525.

* cited by examiner

NANOPARTICLE ASSEMBLIES WITH MOLECULAR SPRINGS

CROSS REFERENCE TO RELATED APPLICATIONS

The present application is the U.S. national phase entry of PCT/US2006/020937 with an international filing date of May 30, 2006, which claims priority to U.S. Provisional Patent Application No. 60/685,741, filed May 27, 2005, both of which are fully incorporated by reference in their entirety.

STATEMENT ON FEDERALLY FUNDED RESEARCH

This invention was made with government support under Contract Nos. CHE-9876265 and BES-0119483 awarded by the National Science Foundation. The government has rights in the invention.

NAMES OF PARTIES TO A JOINT RESEARCH AGREEMENT

Ohio University and The Regents of the University of Michigan are parties to a joint research agreement which covers the subject matter of this invention.

BACKGROUND

Recently, nanoparticle (NP) superstructures have become an important pathway to the creation of smart materials with new functionalities. Most of the current examples of complex NP systems, such as bioconjugates or hybrid nanocolloids and their lattices, are typically static, i.e. have limited response to the environmental parameters and do not exhibit smooth reversible transitions of their 3D organization/geometry in response to external stimuli. Dynamic NP superstructures with gradual structural adaptation to common physical parameters may reveal interesting analogies with biological entities similar in scale. Additionally, such systems can also find technological applications as novel optical devices.

A need exists for new sensor materials with physical dimensions as to require no substrate. This feature will make possible the sensor's utilization in nanofluidic devices and in other strongly confined spaces, where other sensors can not reach. Developing NP assemblies that are soluble in water, one can experimentally measure the 3D property distributions, which may include concentration, temperature, and pH gradients. These data are of critical importance for understanding both chemical and physical processes in confined fluids. Careful design of the superstructure addressing biocompatibility can also produce sensors of monitoring of biological reactions in the confinements of a single cell.

New sensors should have photostability greater than that of organic dyes, which have been used in the luminescent tags, but it is equally important for the long-term observation of biological objects. The processes used by the sensors should be reversible. The sensors should provide high sensitivity and high signal/noise. The sensors should have a wide range of biological selectivity.

SUMMARY OF THE INVENTION

Provided herein are dynamic nanoparticle structures having a first nanoparticle, a second nanoparticle or nanowire, and a molecular spring, wherein the first nanoparticle is connected to the second nanoparticle or nanowire by the molecular spring. The dynamic nanoparticle structures are useful as sensors, having very small physical dimensions and requiring no substrate. The sensors may be used in solutions and incorporated into microchips.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1:
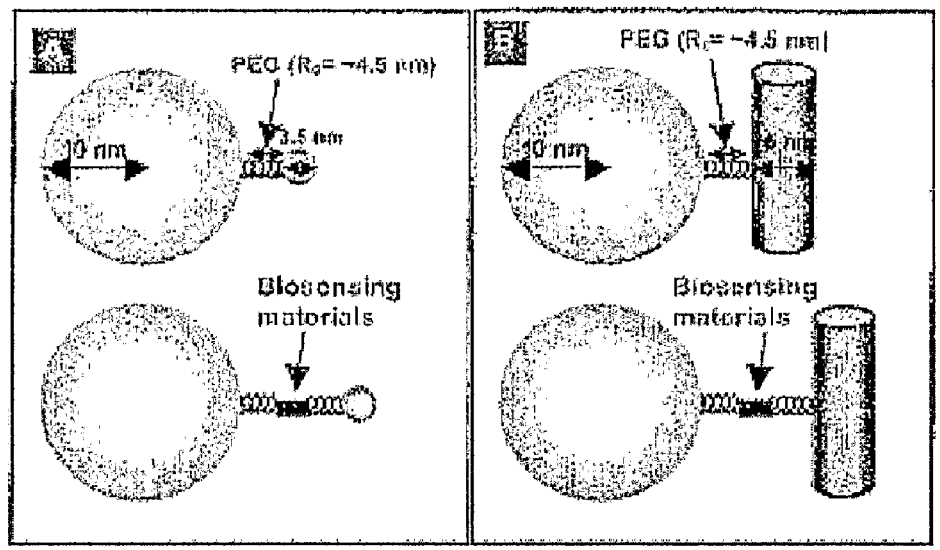
FIG. 1 shows a scheme of nano-hybrid of NPs, NWs, and PEG conjugation.

The following description of the preferred embodiments is merely exemplary in nature and is in no way intended to limit the invention, its application, or uses.

Provided herein are new micro and nano-sensor materials with physical dimensions as to require no substrate. This feature makes possible the sensor's utilization in nanofluidic devices and in other strongly confined spaces, where other sensors can not reach. Using the sensors provided, NP assemblies that are soluble in water, one can experimentally measure the 3D property distributions, which may include concentration, temperature, and pH gradients. These data are of critical importance for understanding both chemical and physical processes in confined fluids. Careful design of the superstructure addressing biocompatibility can also produce sensors of monitoring of biological reactions in the confinements of a single cell.

The photostability of NPs is much greater than that of organic dyes. In the past it was used in the luminescent tags, but it is equally important for the long-term observation of biological objects.

Expansion/contraction processes of molecular spring are reversible, and so are the sensors based on them.

$1/R^6$ dependence of optical effects results in a strong change of emission and therefore in high signal/noise (S/N) ratio and sensitivity. Improvements are also expected from the high intensity of Au-enhanced NPs and nanowires.

Wide range of biological selectivity can be obtained when inserting a biomacromolecule between two molecular springs. The bio-sensing materials can be enzymes, antibodies, nucleic acid fragments, etc.

Wavelength shift based sensor eliminates the need for internal intensity reference. This will both simplify the measurements and make them more accurate and reliable.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

The development of micro- and nanofluidics devices demands in-situ measurements of many parameters in the stream of liquids. Local gradients of solvent concentration, temperature, pH and other parameters have tremendous importance for the development of lab-on-a-chip applications and similar analytical tools. The same problem also appears in biomedical fields that require evaluation of local concentrations and other parameters for intricate geometries of 3D cell scaffolds, which affect the development of cells residing on the scaffolds. Both tasks are difficult to accomplish using traditional sensor deployment schemes, which often require substrate and wires. Imaging of these gradients by confocal microscopy, although possible, but based mostly on fluorescence intensity mapping, extraction of quantitative data from these measurements requires internal intensity standards to account for fluctuations of label concentration, which both complicate the procedure and affect accuracy of the measurements often making it impossible to obtain the absolute value of the parameter of interest. The problem is exacerbated when the degree of confinement of the liquid increases. Sensing mechanisms based on emission frequency shifts, rather than on intensity variations, can significantly improve the technology of micro- and nanoscale sensing. It will tremendously simplify the gradient mapping in fluidic devices and biological materials with liquid flows because the frequency readings can be made independently of the intensity and can be calibrated externally. Micro and nano-scale sensing as described herein may contribute to a variety of technologies and will make possible evaluation of liquid structure in confined spaces on chemical processes, as well as in-situ monitoring of a variety of intracellular processes in single cells.

Excitons generated in semiconductor NPs or nanowires create an oscillating electrical field around a quantum dot, which, in turn, shift the electron gas in Au NPs. When both transitions resonate, i.e. the wavelengths of NP emission and Au adsorption coincide, surface plasmons are created in Au colloid. They generate a strong electrical field in the vicinity, which stimulates electron-hole recombination in the semiconductor particle. The distance change from compression/expansion of molecular springs can secure high sensitivity of emission since exciton-plasmon interactions depend on the distance as $1/R^6$. Surface plasmon intensity on the Au NPs is strongly decreased above a certain distance that depends on the size of NPs, normally, a few nanometers.

Optical processes in superstructures involving nanowires are similar with the exception that surface plasmon also results in the localization of the exciton in the nanowires in the vicinity of the Au NP. Presumably, attraction to the plasmon does not allow the exciton to escape in other parts of the nanowires with narrower band gap and causes, not only the luminescence intensity change, but also a shift in its wavelength. The wavelength shift is exceptionally important for sensing because it can simplify many detection procedures.

Closeness of energy of the Au NP plasmon (549 nm) and CdTe NP exciton (568 nm) produces resonance conditions in the superstructure. Once exciton in CdTe NP is generated, it induces oscillations of electron density in Au NP, i.e., plasmon. The resonance between them has two effects on emission of CdTe. First, it results in enhancement of the luminescence intensity of the NPs. Secondly, it makes luminescence intensity very sensitive to the interparticle distance.

Importantly, the high sensitivity of the NP emission to temperature in our designed superstructures arises from the two factors: (1) P rapidly decreases with the Au—CdTe distance approximately as $R^6$, where R is the average radius of the nanoparticles and (2) the exciton energy is very close to the plasmon resonance that leads to few-fold plasmon enhancement of emission. Compared to other approaches to sensing with nanocolloids, expansion and contraction of the molecular springs represents a very sensitive transduction mechanism for chemical detection: any change in dimensions of superstructure results in a shift of the plasmon resonance with respect to the exciton energy and in a subsequent reduction of the enhancement factor.

Thus the CdTe-PEG-Au system exemplifies a nanoscale superstructure with reversible structural adaptability to the environmental conditions. The combination of this property with plasmon-exciton interactions displaying high sensitivity of the optical output on the distance modulations can be put in the foundation of a new family of sensing and optoelectronic devices.

Described herein are nanoscale sensing devices from different types of nanoparticles (NPs) and nanowires (NWs) connected by molecular springs. The distance between the nanoscale colloids reversibly changes depending on conditions or analyte concentration and may be evaluated by fluorescence measurements. Data indicate that both high emission intensity variations and frequency shift can be obtained in such systems.

As a practical demonstration of the capabilities of the new technology, we created NP assemblies applicable for direct imaging of solvent and temperature gradients in fluidic devices. Additionally, we carried out the imaging of chemokine gradients in 3D scaffolds with frequency shift sensing. Although the localized gradients of chemokines in the immunological system is extremely important for fundamental immunology and development of new treatment methods for the immunoimpaired patients, the lack of appropriate technology made it difficult. Success demonstration of the chemokine gradient with absolute concentration mapping will have broad impact on the understanding and treatment of many illnesses including irregular angiogenesis, rheumatoid arthritis, human hepatocellular carcinoma, Type 1 diabetes mellitus, and some forms of cancers.

Nanohybrid systems described herein may be described by the schematics in FIG. 1. Two different nanoscale entities (NP±NP or NP+NW) are connected to each other by the oligomers, such as PEG, which can expand and contract depending on the conditions. The PEG linkers are connected to the nanocolloids by its terminals, which creates a structure that can be characterized as a molecular spring. Using the methods described herein, one can create a covalent bond between a NP and a specific end group in the PEG chain. In order to impart the biological selectivity of the sensor, one may incorporate either a protein, DNA linker, or other molecule or macromolecule of interest. The binding event will cause the change in interparticle distance as well.

Sensing in such assemblies is based upon optical transduction of the PEG conformational changes. The latter can be caused by (a) phase transition in PEG, (b) variation of particle attraction to each other or (c) binding events. Optical effects originate from the plasmon-exciton interactions. It is well known that surface plasmons on Au and Ag NPs induce strong surface enhanced Raman scattering (SERS). Recently, it was also demonstrated that Au NPs induced more than 5-fold enhancement of PL with high blue shift of emission wavelength. In the first approximation, the mechanism of luminescence enhancement is similar to SERS. The electronic nature of the optical transitions in NP, strong resonant component, and quantum effects, necessitate the development of a new theoretical approach, which were carried out in this project. In simple terms, the luminescence enhancement in superstructures in FIG. 1 can be described in the following way. Excitons generated in semiconductor NPs or NWs create an oscillating electrical field around the quantum dot, which, in turn, shift the electron gas in Au NPs. When both transitions resonate, i.e., the wavelengths of NP emission and Au adsorption coincide, surface plasmons are created in Au colloid. They generate a strong electrical field in the vicinity, which stimulates electron-hole recombination in the semiconductor particle. The distance change from compression/expansion of molecular springs can secure high sensitivity of emission since exciton-plasmon interactions depend on the distance as $1/R^6$. Surface plasmon intensity on the Au NPs is strongly decreased above a certain distance that depends on the size of NPs, normally a few nanometers.

Optical processes in superstructures involving NWs are similar with the exception that surface plasmon also results in the localization of the exciton in the NWs in the vicinity of the Au NP. Presumably, attraction to the plasmon does not allow the exciton to escape in other parts of the NWs with narrower band gap and causes, not only the luminescence intensity change, but also a shift in its wavelength (see below). The wavelength shift is can simplify many detection procedures used with the sensors described herein.

Discussing the concept of hybrid nanocolloid assemblies, we want to point out the following advantages and features of this molecular system as sensing devices.

First, this system has small physical dimensions and requires no substrate. This feature makes possible its utilization in nanofluidic devices and in other strongly confined spaces, where other sensors cannot reach. Since the NP assemblies in FIG. 1 are soluble in water, one can experimentally measure the 3D property distributions, which may include concentration, temperature, and pH gradients. These data are important for understanding both chemical and physical processes in confined fluids. Careful design of the superstructure addressing biocompatibility can also produce sensor of monitoring of biological reactions in the confinements of a single cell.

Second, the photostability of NPs is much greater than that of organic dyes. In the past it was used in the luminescent tags, but it is equally important for the long-term observation of biological objects.

Third, expansion/contraction processes of molecular spring are reversible, and so are the sensors based on them.

Fourth, $1/R^6$ dependence of optical effects results in a strong change of emission and therefore in high signal/noise (S/N) ratio and sensitivity. Improvements are also expected from the high intensity of Au-enhanced NPs and NWs.

Fifth, a wide range of biological selectivity can be obtained when inserting a biomacromolecule between two molecular springs. The bio-sensing materials can be enzymes, antibodies, nucleic acid fragments, and so forth.

Sixth, wavelength shift based sensor can become a marked improvement over intensity-based sensors because they eliminate the need for internal intensity reference. This will both simplify the measurements and make them more accurate and reliable.

Recent advances in the organization of functional NP-biomaterial/polymer hybrid systems in our laboratory induced novel technology to assemble electronic, electrochemical, and photo-electrochemical sensing devices. The nano-assembly technique is a promising tool for precise or fuzzy construction of micro/nanostructures depending on specific purposes to realize sensing devices. The interaction of plasmon-exciton in the nano-hybrids has been scrutinized based on the Au NPs and CdTe NPs/NWs system. First, the static nano hybrids of NPs and NWs conjugation with biomolecules was theoretically explained to calculate the enhancement factor due to Au NPs. The enhancement factor that may be originated from the increase of incident electromagnetic field (at laser=420 nm) or from the increase of radiative probability of NW-excitons (at about 660 nm) was calculated about 6.5 when Au NPs are surrounded on the surface of nanowires. To understand optical phenomena in NP-NW superstructures, the ideal model of conjugate structures was used. The Au NPs around the central CdTe NW can be viewed as a shell. This model described the limiting case when the Au NPs covered the entire surface of NW and responded collectively on the incident electromagnetic field. The collective character of the response was practically important since the electric field enhancement factor can increase the efficiency of laser devices and expand the working range of NP sensors. Since the peak position, not shown, is close to the position of the fluorescence peak (at emission=660 nm), the main contribution to the calculated enhancement factor came from the increase of emission probability, which correlated very well with the fact that the lifetimes of the NWs, after conjugations, were substantially shortened. This research was of fundamental importance to figure out special electric and optical properties of nanoscale superstructures that are assembled from metallic and semiconducting NPs and NWs.

The theoretical comprehension of the static nano hybrid expanded to make a model of dynamic nano hybrid with molecular spring using PEG polymer in which the radius of gyration (Rg) of PEG was the distance between two nanomaterials. Rg was varied depending on the hydrophilic and hydrophobic properties of solvents. A theoretical model based on the experimental results was utilized to reveal the physical bio-sensing mechanism of dynamic nano hybrids with molecular spring leading to the solvent-sensitive optical responses. The emission intensity of the NW in the presence of metallic nano-shell was proportional to the product of electromagnetic field intensities that were calculated. It was acknowledged that the emission of NW in our samples was strongly enhanced due to plasmon resonance and the stretching of PEG moved the system away from the exciton-plasmon resonance resulting in the suppression of emission. A theoretical model explained the origin of PL changes in the dynamic nano hybrid system where plasmon resonances and plasmon-enhanced PL were very sensitive to any nano-mechanical movements/deformations. The described optical phenomena represented a novel mechanism for biosensors with optical read-out.

A more complicated model would be of necessity to explain similar optical phenomenon depending on other external sources in an aqueous state. Currently, we prepared a dynamic NP hybrid that responded to the temperature change in an aqueous solution and explained theoretically its optical property of luminescence. Two different NPs i.e., Au NPs with 20 nm of diameter, and CdTe NP with 3.5 nm of diameter, were utilized to prepare nanohybrids in an aqueous solution. Theoretical calculations demonstrated that the change in the PEG-controlled distance between NPs was the cause of the observed modulations in emission intensity.

The PEG we used here for the molecular spring between nanomaterials has a number of unique properties that are directly related to the presence of repulsive interactions, which give it a distinctive capability of structure mobilization. The (11/2) helical conformation of PEG can be altered with the response of thermodynamic energy since the melting temperature (Tm) of this PEG is 50-60° C. Based on the literature data, it is known that the radius of gyration, Rg of PEG with M.W. 3400 constitutes 20-30% of the polymer globule volume ratio in the 20-60° C. range within 10 min. The conformation of PEG also changes in different solvents. The coiling of the PEG backbone becomes more extended in "good" solvents like ethanol and shorter in "bad" ones like water. It is known that PEG coils in an aqueous solution are larger and PEG coil-coil interactions are stronger than those found for typical polymer coils in organic solvents because the unusually large size and long range of PEG coil-coil interactions in water are due to the unusual ability of water molecules to pack into and swell coils along with a general structuring of water in the PEG-H20 system, respectively.

Among others, this work targeted utilization of NP+NP and NP+NW hybrid superstructures for bio-sensing. This necessitated addressing the issue of biocompatibility of NPs. Semiconductor NPs, such as CdS, CdSe and CdTe (aka, quantum dots), have been introduced as new fluorophores due to their greater and longer fluorescence. The improvement on synthesis of water-stable NPs and Centrifuged bio-labeling techniques lead to various conjugation techniques to specific biomolecules; e.g., endocytic uptake of NPs and selective labeling of cell surface proteins with NPs conjugated to antibodies. These technological advances triggered the recent explosion in their use in biological imaging, immunostaining, and sensing. Analysis of available literature showed that there is no final decision about their toxicity. A number of groups have suggested that semiconducting NPs are cytocompatible, at least, with some immortalized cell lines. If the liberation of free $Cd^{2+}$ ions due to deterioration of the CdSe lattice can be prevented, the NPs become quite inert from the point of view of the cells. The cytotoxicity of NPs can be remarkably decreased by optimizing processing parameters such as synthesis, exposure to UV light, and surface coatings. For example, the use of a core-cell structure like silanized CdSe/ZnS nanocrystal-peptide provides a new nontoxic, long-term imaging platform for observing nuclear trafficking mechanisms and cell nuclear processes in the imaging of the nuclei of living cells. The encapsulated luminescent NPs with polymers, including PEG, opened sensitive and multicolor fluorescence imaging of cancer cell in vivo. In one embodiment, Cd-containing NPs are used for biosensing. In embodiments in which a very high level of biocompatibility is required, Si or ZnO NPs or NW may be used. The grafting of poly acrylic acid on the surface of silicon nanoparticles has been used to prepare a stable aqueous luminescent silicon nanoparticle solution. With some modifications, the concept of both molecular springs and plasmon-exciton interactions are applicable to these nanocolloids as well.

Au NPs are prepared by the widely accepted method using citric acid and cetyltrimethyl anunonium bromide (CTAB) as stabilizers. It results in NP dispersions with narrow size distribution and high stability in a wide range of temperatures and pHs. To make conjugation to PEG possible, the original stabilizers may be exchanged with thiols and can be terminated either by any functional groups, for instance, —COOH or —$NH_2$. After that, virtually any kind of spacers can be linked on the surface of Au NPs.

Figure 2:
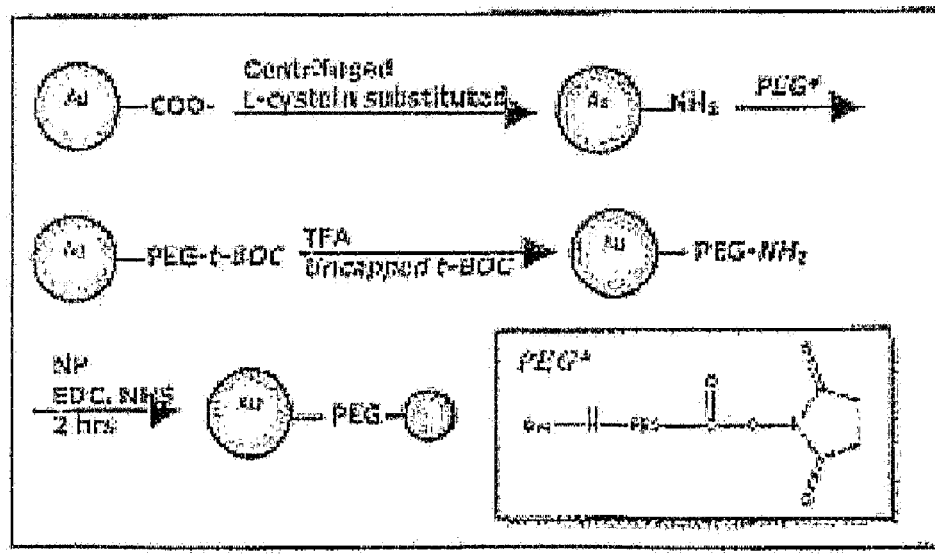
FIG. 2 shows a schematic example of experiments for conjugation with PEG tethered NP's.

Aqueous transparent solutions of CdTe NPs/NWs with high PL, capped with the stabilizers of thioglycolic acid or L-cysteine, are routinely prepared in our laboratory. Their synthesis is described elsewhere. The molecular spring may be an oligomer or polymer that is capable of expansion/contraction processes that may be measured. Preferably, the oligomer is chosen such that the expansion/contraction processes are reversible, thus making the sensors based on them reversible. In one embodiment, PEG with two functional groups at each end, M.W. 2,000–20,000 Da, produced by Nektar Co. USA, may be utilized as a molecular spring between two different NPs. This particular PEG product has two different functional groups. N-hydroxy-sulfosuccinimide (NHS) in one end of PEG chains is a removing functional group when amine group is reacting. The other terminal has a blocking group, t-butoxycarbonyl that can be removed when needed by trifluoric acid (TFA) for further conjugation reactions with NPs. This heterofunctional PEG offers many opportunities for tethering, cross-linking, and conjugation. To link polymeric ligands on Au NPs and CdTe NP, a common EDC/sulfo-NHS zero-length cross linking procedure may be utilized in both cases in which the half-life of the carboxylic group can be extend up to hours to react with amine source. FIG. 2 presents an example of the experimental procedure of tethering PEG to two types of NPs as described herein. Preliminary UV-vis spectra data indicate that PEG tethered Au NPs have surface plasmon absorbance, slightly red shifted and broadened. TEM, AFM, and high-resolution SEM may be used to determine the average number of NPs conjugated to each other depending on the conditions. Cryo-TEM set-up will be used to determine the conformation of the superstructures in the solution state. These data may be obtained for PEG molecules of different molecular lengths and for different experimental conditions (solvent composition, pH, ionic strength, analyte concentration, etc.). The structural data may be correlated with the optical properties. Plasmon-exciton interactions are investigated by using steady-state and time-resolved fluorescence spectroscopy by using Fluoromax and Fluorolog Tau-3 (Jobin Yvon SPEX Horiba, New Jersey).

The synthetic procedure described above for superstructures made from two different NPs may be extended to NWs and NP of different sizes (both Au and CdTe). In one embodiment, a library of superstructures with a variety of structural characteristics and potential expansion-contraction ranges of molecular springs may be produced. This library may then be used to optimize the sensing properties. In some embodiments, molecular spring linkers other than PEG, such as siloxane derivatives may be used. PEG is convenient and applicable to a wide range of conditions typically encountered in micro- and nanofluidic systems, however, it is important to recognize that other molecular springs may be used at complementary temperature ranges or more hydrophobic solvents. Siloxanes can also be helpful in reduction response time of the sensor.

This team has recently demonstrated that the emission intensity of the Au—CdTe complex can be strongly enhanced due to plasmon resonances in the Au sub-system. Plasmon resonances in Au-NPs result in the enhancement of photonic fields inside the CdTe nanocrystals. In the Au-NP-CdTe-NW superstructures the Au-NPs act as an amplifier of photonic fields whereas the CdTe-NW plays a role of optical emitter. For a superstructure made from Au NPs tethered to CdTe NW, the Au corona was approximated as a continuous cylindrical Au-shell. As for CdTe component, we computed their energy structure and wave functions of semiconductor nanocolloids on the basis of multi-band effective mass theory. The exciton-plasmon interaction comes from electric fields inside a superstructure and is described by inter-band matrix elements: $\langle \psi_f | d \cdot E | \psi_0 \rangle$, where E is the electric field inside the CdTe nanocrystal, d is the dipole operator, and $\psi_{0(f)}$ are the initial and final states of the CdTe nanocrystal. The field should be calculated with taking into account the plasmon resonance. The above matrix element and the probability of inter-band transitions in a CdTe NW/NP will be enhanced in the regime of plasmon resonance due to the plasmon-enhancement of electromagnetic fields in/around the superstructure. The electromagnetic fields will be found from Maxwell's equations combined with the equation of the density matrix for the CdTe NP/NW.

Comparison of the theoretical calculations Wavelength film of the luminescence enhancement factor and the experimental data demonstrated very good agreement. Two important points need to be made considering the optical properties of the structures in question: (1) the luminescence enhancement effect comes from the collective response of many Au-NPs, (2) the emission intensity is very sensitive to geometrical sizes of a superstructure, and (3) the wavelength of emission of the semiconductor sub-system depends on inter-nanocrystal interactions. These facts, established on the basis of the theoretical treatment described above, confirm the potential of these systems for sensing. When linkers connecting the nanocolloids in these superstructures are made of temperature- and environment- or analyte-sensitive linkers (see below) capable of contraction/expansion cycles (such as PEG), the optical emission (intensity and wavelength) becomes very sensitive to the chemical content and physical parameters of the solution.

Figure 3:
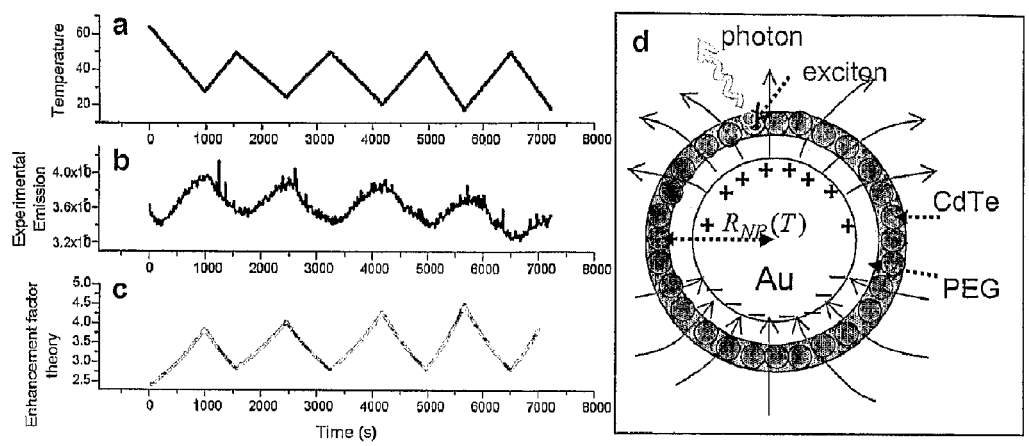
FIG. 3 shows PL intensity variation of PEG tethered Au and CdTe NPs depending on temperature: a, temperature b, PL intensity, c, calculated photon-field enhancement factor of CdTe NPs as a function of time, and d, pictorial representation of the dielectric model used for calculation of curve c and the plasmon excitation with associated field lines; the plasmon excitation inside a Au nano-sphere interacts with excitons in CdTe-NPs through electric fields. The distance RNP(T) varies with temperature.

The shell approximation can be applied to the layer of CdTe NPs surrounding a larger Au sphere (see FIG. 3). Theoretical calculations, according to the outlined scheme, also demonstrated good agreement with experimental results. Besides the fact that the theoretical description of plasmon-exciton interactions can be applied to superstructures of different morphologies, this system can be use to exemplify how the theory of plasmon-exciton interactions will be applied to the description of sensing processes in molecular spring superstructures, In this structure, the Au-sub-system serves as an amplifier and when the Au—CdTe distance increases the emission intensity decreases (FIG. 3c). The polymer linker determines the Au—CdTe distance and becomes expended or compressed with temperature or certain solvents. At the same time, the wavelength of exciton emission of CdTe-NW/NP changes since the strength of interaction between excitons and plasmons varies. This mechanism will be used to realize "the wavelength shift sensors". The emission intensity and wavelength are very sensitive to spatial expansion or shrinking of a CdTe—Au structure because the inter-nanoparticle interaction rapidly changes with distance (typically as $1/R^6$). This interaction comes from long-range Coulomb coupling between NPs and NWs.

The dielectric and optical properties of Au—CdTe superstructures are combined with the chemical characteristics of the polymer linker. The sensing properties will enter our model through geometrical distance between Au-NPs and CdTe-NW/NP; this distance is a function of temperature or concentration of certain chemicals in a solution (methanol, ethanol, etc). Calculated electromagnetic fields in complexes with the polymer linkers become strongly sensitive to temperature and solvent concentration. The system of equations to solve in this project will incorporate the Maxwell's equations, the equations of motion of density matrix of individual CdTe-NPs, and the thermal equations. In parallel to electromagnetic-field calculations, we will study the quantum mechanical mechanisms of energy exchange and dissipation inside the Au-NP-PEG-CdTe-NP superstructures. The energy dissipation mechanisms are especially important; several other groups observed that the Au-NPs can suppress optical emission of luminescent molecules or semiconductor NPs. The likely mechanism of dissipation is energy transfer to and dissipation in Au-NPs. The emission wavelength of superstructures depends on the strength of exciton-plasmon interaction.

Theoretical assessment of the optimal structure for sensing will be carried out in the following way. From the description above, one can see that placement of Au and CdTe species cannot to be too close or too far away. In the first case, the change in the length of the molecular spring will be too small to have noticeable optical effects and high S/N ratio. The penetration of analyte to, for instance, biologically sensitized linkers will be frustrated in this case. Wide gap between Au and CdTe will also mean small optical effects because of the fast decay of the plasmon-exciton interactions (see Eq. 2) and small S/N as well. Thus, theoretical calculation with estimated diameters of the PEG, proteins, DNAs, as well as NPs and NWs, provide us with the estimate of the optimal distance, which will be then matched by the components of the superstructure to be assembled as described herein. Additionally, we can minimize energy dissipation and maximize sensitivity of sensor operation due to inter NP energy transfer, which may also be carried out with similar computational models.

CdTe-PEG-Au superstructures exemplify a nanoscale system with reversible structural adaptability. These will allow simple acquisition of gradient maps in micro- and nanofluidics devices and other confined fluidics systems, where conventional sensors cannot be deployed. This will make possible better understanding of thermal and molecular transports at nanoscale. For example, nano hybrid of Au NPs and CdTe NPs/NWs with PEG conjugation reveals variations of CdTe luminescence intensity when temperature is varied between 20-60° C. The conformation of PEG is altered with the response of thermodynamic energy in the media, which should produce concomitant change in the luminescence output. The superstructure showed clear reversible temperature dependence of the PL intensity (FIG. 3a, b).

Remarkable conformation change of PEG on hydrophilic and hydrophobic solvents will be an opportunity to develop nano optical sensor to measure solvent composition maps in fluid streams. Preliminary data using NP-PEG-NW superstructure measured luminescence intensity response after the transfer of an aliquot of the superstructure from water to methanol, ethanol, and 2-propanol. The PL change depending on the solvent, can explain the distance variation between NPs and NWs due to the conformation change of PEG chains induced to change interaction between the plasmons of NPs and the excitons of NWs.

On the basis of the theoretical calculations of the optical effects, the optimal combination of the following parameters may be chosen: diameter of Au NPs, diameter of CdTe NPs or NWs, geometry of the system (i.e., either CdTe NPs or NWs), length of PEG, the density of PEG linkages on the base colloid, and wavelength of excitation/registration. The library of different conjugates to be used for the validation of the calculations may be taken advantage of to achieve this objective. To accomplish this objective, a simple model of a Y-type channel microfluidics device will be made in our clean-room facilities from silicon substrate capped with a glass slide. One solvent will be fed in one arm of Y, while the other one is fed in the other arm. Formation of the gradients after the mixing in the bottom part of Y will be imaged for different fluid flows and sizes of the channels. The flow rates to be used will be relatively slow. The same experiment will be repeated for feeds with different temperature and chemical composition.

Eventually, flow obstacles will be made in the joint channel to cause mixing. The mapping of the gradients will be carried out by a confocal or fluorescent microscope.

In other embodiments, the sensors provided herein may be used for the evaluation of pH and ionic strength of the fluid stream. CdTe luminescence displays strong sensitivity to the pH of the media. Additionally, the variation of pH will change the electrostatic repulsion/attraction balance between CdTe and Au colloid, which will reversibly change the expansion of the PEG spring. Therefore, one can expect that the intensity of the superstructure emission will depend on the local pH. This effect will be further enhanced by the plasmon-exciton interactions, which may produce an exceptionally sensitive luminescence pH probe. This objective is relevant not only as a tool for microfluidics, but also as a source of intracellular processes, which we are considering for the next phase of this project. To have exclusive selectivity on nano hybrids, sensing materials such as DNA fragments and proteins may be technically conjugated in nano hybrids as described in FIG. 1. Using the same bioconjugation reactions, as depicted in FIG. 2, used to attach PEG to biomaterials, complex hybrid structures Au-PEG-DNA-PEG-CdTe and Au-PEG-mAb-PEG-CdTe may be prepared. With exclusive interactions of conjugated bio-sensing materials to targeting biomaterials by ligand-receptor, antigen-antibody, or DNA hybridization, combined sensing parts and linked PEG chains will change their conformation, which will induce the alternation of exciton-plasmon interaction. This property will be employed here to create the chemokine sensitive superstructures described above. This indirect optical measurement of gradient will not only to avoid critical problem on purification step, but also to obtain high selectivity and sensitivity of reliable data.

Wavelength Sensors from NP-NW Systems Intensity-based sensors work very well for establishing relative distribution maps. But they also have a significant disadvantages. The change of the luminescence intensity from either presence of analyte or concentration variations of the sensing molecule cannot be distinguished. The readings of emission intensity also depend on the light collecting optics in the registration system. All this requires incorporation of standards, strict control over experimental set-up, and often an assumption of uniform label distribution in a particular area. Therefore, wavelength based sensors have much greater utility. In the superstructure of CdTe NW-PEG-Au NP, the wavelength shift was observed to be over 20 nm with fair linearity when temperature was varied between 20 and 60° C. (data not shown). Importantly the effect was completely reversible. Considering that the spectral resolution of even inexpensive spectrometers can be 0.1 nm, the wavelength shift of 20 nm will be sufficient for many analytical purposes. The superstructures described here may produce a versatile platform for wavelength-based sensing of many compounds.

The current hypothesis for the wavelength dependence of the luminescence in PEG conjugates with NWs is the following. The electrical field generated around Au NPs results in enhanced localization of the exciton in the NWs due to electrostatic attraction of the two dipoles. Without the plasmon generated, the exciton diffuses along the wire and can emit in a different place. During the diffusion the exciton may encounter the part of NW with slightly larger diameter, and thus smaller bandgap, which will result in the preferential emission from this part of the NW. Our recent results with NP chains confirm this point. When the plasmon is acting on the exciton, the one-dimensional diffusion of exciton along the NW is frustrated, and thus, the emission occurs in the close vicinity of Au NP. Potentially there could be other effects related to plasmon-exciton interaction leading to the dependence of the energy of the emitted quanta on the PEG extension. The exciton diffusion hypothesis will be tested both experimentally and theoretically. The superstructures will be created where the density of PEG linkers on the NW will be varied. As well, we will monitor the wavelength shift of plasmon-exciton interaction on NP-NW depending on the polymer length and the diameter of the Au NP attached, which will affect the strength of plasmon-exciton coupling. The corresponding structures will be investigated by luminescence spectroscopy and microscopy.

Demonstration of the Applicability of the Molecular Spring Hybrid Sensors to the Measurements of Local Gradients of Chemokines in a 3D Scaffold Understanding gradients of chemokines (i.e. signal proteins which stimulate the movement of dendritic cells toward the source of chemokines) in tissues of immune system is a central problem for many immune system malfunctions. For example, the expression of chemokines gradient regulates the rate and pattern of inflammatory cell accumulation in immune system of brain damage. It is also important for replication of some immune system organoids in three-dimensional scaffolds. Therefore, quantitative measurements of local concentrations of chemokines in 3D scaffold represent an important fundamental problem which can be resolved with the use of suggested sensor system. As a model we will use an inverted colloidal crystal scaffolds made from hydrogel, which were recently developed in our laboratory. They have highly ordered structure convenient for model studies and high transparency. Their topology is reminiscent of the 3D matrixes in bone marrow and thymus. It prevents deployment of traditional sensors in it.

To construct gradient sensors for this task we took advantage of antibodies to chemokines, i.e., a superstructure with the following composition was created: NP-PEG-antibody-PEG-NP/NW following the schematic in FIG. 1. A reactive carbonyl group in PEG was generated in place of the terminal amino group of protein where one terminal of PEG is already conjugated with NPs or NWs. The N-terminal-introduced reactive carbonyl group specifically reacts, under mild acidic conditions, with an aminooxy-functionalized PEG to form a stable oxime bond. Using polymers of different size and shape (linear or possibly multibranched), various conjugates with respective murine chemokine antibody was produced. For instance, one can use MIP-2, which sends a signal of inflammation, and TCK-1, which is an important signal protein of thymus, as test system for gradient sensing. Both chemokines and antibodies for them are available from R&D Systems, Minneapolis.

When the NP-PEG-antibody-PEG-NW system encounters the chemokine, the antibody-antigen binding event will occur, which will result in increase of the distance between Au NP and CdTe NW, which will be detected by the wavelength shift as well as by intensity change. Different concentrations of a chemokine, for instance TCK-1 may-be first tested in non-gradient solution and calibration curve will be created. The response may be also be optimized to obtain the strongest possible wavelength shift. Subsequently, the scaffold will be immersed in the solution containing the suspension of our sensor and a drop of chemokine will be placed on one side of the 3D scaffold. When the gradient of TCK-1 is established, the scaffold will be imaged by confocal microscopy to verify the luminescence of the sensor. After that, we shall focus the microscope on small (1-5 micron) parts of the scaffold in different areas. A portion of light from the acquisition channel will be diverted to the spectrometer through the optical fiber provided by the microscope manufacturer (Leica, Germany). The spectra of the sensor in different parts of the scaffold will be analyzed and compared to the experiment in non-gradient solution. The actual concentration of chemokines in different places of the 3D scaffold and at a different distance from the place of chemokine introduction may then be determined. This experiment will provide a foundation for the spectral mapping of the chemokine and other gradients in complex 3D fluidic systems.

Nanoparticle Assemblies with Molecular Springs: Nanoscale Thermometer Another embodiment of the sensors described herein is reversible nano-thermometer built from two types of NPs connected by a polymer molecule acting as a molecular spring. The underlying microscopic mechanism of the nano-thermometer involves the plasmon resonance and exciton-plasmon interaction.

Figure 4:
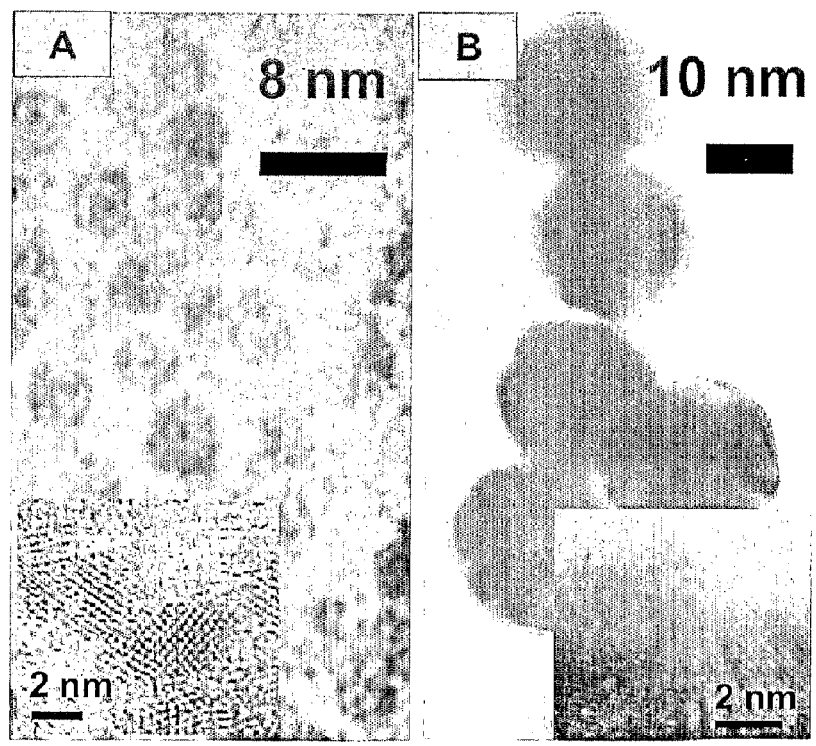
FIG. 4 shows the images of transmittance electron microscopy; a, CdTe NPs, and b, Au NPs. The inserts present the high resolution lattice plane images of nanoparticles. The d-spacing of CdTe and Au NPs were measured 0.352±0.3 nm, 0.23±0.008 nm, respectively.

The system was excited with He:Ne laser at 633 nm (20 mW, Uniphase, USA). The red light quanta result in two photon excitation of CdTe NPs. Closeness of energy of the Au NP plasmon (549 nm) and CdTe NP exciton (568 nm) produces resonance conditions in the superstructure. Once exciton in CdTe NP is generated, it induces oscillations of electron density in Au NP, i.e., plasmon. The resonance between them has two effects on emission of CdTe. First, it results in enhancement of the luminescence intensity of the NPs. Secondly, it makes luminescence intensity very sensitive to the interparticle distance. Within a certain range of distances, the reduction of the gap between the particles causes enhancement of CdTe luminescence at 568 nm. The high resolution transmittance electron microscopy shows the internal organization of this superstructure (not shown). CdTe colloid can be identified by the lattice plane spacing, d, equal to 0.352±0.3 nm that is typical for cubic CdTe. The Au NPs showed d=0.23±0.008 nm, which corresponds to the (111) planes of Au crystal (FIG. 4. These images present that many smaller CdTe NPs are attached to the surface of larger Au NP forming a nanoscale assembly resembling cellular flagella.

The temperature of CdTe-PEG-Au dispersion was varied between 20-60° C. by a heating/cooling circulator (NESLAB, EX-111, USA). The conformation of PEG can be altered with the response of thermodynamic energy in the media since the melting temperature (Tm) of this PEG is 50-60° C. This results in the change in distance between the particles, which should produce concomitant change in the luminescence output. Indeed, the superstructure showed clear temperature dependence of the PL intensity.

Higher temperature leads to a decrease in luminescence due to more extended conformation of PEG chain and vice versa (FIG. 3a, b). Non-PEG bonded system did not present any temperature dependence. Importantly, the process is totally reversible showing less than 10% of photodegradation every temperature cycle (1500 sec).

Theoretical calculations demonstrate that the change in the PEG-controlled distance between the NPs is the cause of the observed modulations in emission intensity. The photon-field enhancement factor, P, inside the CdTe NPs determines the probability of photon emission by an exciton trapped in a CdTe NP, and therefore, the emission intensity is proportional to the factor P:

$$P(\omega, R_{NP}) = \langle E^2 \rangle_\Omega / E_0^2 \tag{1}$$

where $E_0$ is an external electric field inside a CdTe NP in the absence of the Au-subsystem, E is the electric field in the presence of Au-NP averaged over solid angle $\Omega$, $R_{NP}$ is the position of the CdTe NPs with respect to the center of the superstructure (FIG. 3d), and $\omega$ is the laser frequency. We will use here a simplified theoretical model which approximates a granular, molecular spring superstructure as an Au sphere surrounded by polymer and CdTe shell (FIG. 3d). Mathematical treatment of all CdTe NPs individually could be useful but requires sophisticated numerical simulations. At the same time, a simple shell model can reveal the physical essence of the phenomenon. Note that the majority of Au NPs are seen to be faceted (4 FIG. 4). While being mindful of the potential electrical field aberrations caused by face edges, we consider them as secondary effects in comparison to the model approximation.

Thus, treating Au NPs as spheres we can analytically calculate the electric fields induced around the Au NP by matching the electrical boundary conditions and involving the first spherical harmonics. After averaging over, we obtain $$P(\omega, R_{NP}) = B + 2C/R_{NP}^6 \tag{2}$$

where B and C are complicated functions of the dielectric constants of the metal ($\in_m(\omega)$), PEG ($\in_0$), and CdTe ($\in_{CdTe}=8$). In addition, the coefficients and depend on the radii of the spherical shells in our model. The function $\in_m(\omega)$ for Au NPs was taken from the work of Quinten, described elsewhere. The effective constant of surrounding media $\in_0$ was determined to be 3.4 from the comparison of the calculated and measured Au plasmon peak positions in the absorption spectra (not shown). The value of $\in_0$ is larger than that of water ($\in_{water} \sim 1.8$) because of the presence of polymer chains around the Au NP with a greater dielectric constant. $R_{NP}$ is determined by the radius of gyration of PEG, $R_{PEG}$. Based on the literature data, $R_{PEG}$ of PEG with M.W. 3400 is 2-4 nm. The temperature induced changes in the 20-60° C. range constitute 20-30% of the polymer globule volume ratio, i.e., changes in RPEG of 0.6-1.2 nm·16 Assuming linear dependence RPEG (T)=3 nm+1 nm (T−30° C.)/30° C., one can arrive to $$R_{NP}(T) = 11.8 \text{ nm} + RPEG(T) = 14.8 \text{ nm} + (T-30° \text{ C.})/30° \text{ C.} \tag{3}$$

Importantly, the high sensitivity of the NP emission to temperature in our designed superstructures arises from the two factors: (1) P rapidly decreases with the Au—CdTe distance (approximately as) and (2) the exciton energy is very close to the plasmon resonance that leads to few-fold plasmon enhancement of emission. Compared to other approaches to sensing with nanocolloids, expansion and contraction of the molecular springs represents a very sensitive transduction mechanism for chemical detection: any change in dimensions of superstructure results in a shift of the plasmon resonance with respect to the exciton energy and in a subsequent reduction of the enhancement factor. Substitution of RNP (T) into the equation for P($\omega$,$R_{NP}$) for h$\omega$=2.2 eV corresponding to 568 nm resonance wavelength gives analog of the experimental I(T) curve calculated in terms of photon-field enhancement factors (FIG. 3c). The amplitude of the temperature zig-zag for P($\omega$,RNP) is ca. 30%. This correlates very well with variation of emission intensity in our experiments (FIG. 3a, b). The slightly lower amplitude registered in the experiment can be attributed to steric hindrance in the CdTe corona around Au NP preventing the formation of a perfect CdTe-NP shell assumed by our model.

Thus the CdTe-PEG-Au system exemplifies a nanoscale superstructure with reversible structural adaptability to the environmental conditions. The combination of this property with plasmon-exciton interactions displaying high sensitivity of the optical output on the distance modulations can be put in the foundation of a new family of sensing and optoelectronic devices.

Experimental CdTe NPs 3.7 nm in diameter with emission at 568 nm were conjugated to a flexible spacer, poly(ethylene glycole) oligomer (PEG), and then linked to 20 nm Au NPs with surface plasmon peak at 549 nm forming a molecular spring type structures. The level of structural control necessary to produce molecular spring assemblies from NPs, rather than disorganized aggregates, was possible because PEG oligomer had two different functional groups in the ends of the chain, t-BOC-NH-PEG-COO-NHS (M.W., 3400 Da, Nektar, Ala.), where NHS and t-BOC stand for N-hydroxysulfosuccinimide and t-butoxycarbonyl groups, respectively. The stabilizer, cetyltrimethylammonium bromide (CTAB, Aldrich, Milwaukee, Wis.) of Au NPs was substituted to L-cysteine (Aldrich, Milwaukee, Wis.) in order to obtain —NH2 functional group. PEG of 10 mg was dissolved in deionized water of 560 μL and dimethyl sulfoxide (DMSO) of 140 μL. This PEG solution of 700 μL was mixed with the Au NPs solution of 700 μL and left it at room temperature for 12 h with gentle stirring. This procedure resulted in conjugation of —NHS terminus with —$NH_2$ group of the NP stabilizer via covalent amide linkage. After that the t-BOC protection of the other end of PEG was removed by standard treatment with 5 μL of trifluoric acetic acid (TFA) for 20 min. The regenerated —$NH_2$ terminus of PEG can be conjugated to CdTe NPs via standard conjugation techniques i.e., EDC/sulfo-NHS cross linking procedure, resulting in covalent attachment of CdTe to the PEG chain on the end opposite to Au NP.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A dynamic nanoparticle structure comprising:
a first nanoparticle;
a second nanoparticle; and
a molecular spring, and wherein:
the first nanoparticle is connected to the second nanoparticle by the molecular spring;
the first nanoparticle comprises a metallic nanoparticle;
the second nanoparticle comprises a semiconducting nanoparticle, the semiconducting nanoparticle selected from the group consisting of Cd, CdS, CdSe, CdTe, Si, ZnO and combinations thereof; and
the molecular spring comprises PEG and derivatives thereof.

2. The dynamic nanoparticle structure of claim 1 further comprising a biosensing material attached to the molecular spring and residing between the metallic nanoparticle and the semiconductor particle.

3. The dynamic nanoparticle structure of claim 2 wherein the biosensing material is selected from the group consisting of enzymes, antibodies, nucleic acid fragments, and proteins.

4. The dynamic nanoparticle structure of claim 3 wherein the structure is water soluble.

5. A dynamic nanoparticle structure comprising:
a nanoparticle;
a nanowire; and
a molecular spring, and wherein:
the nanoparticle and the nanowire are connected by the molecular spring;
the nanowire comprises a semiconducting nanowire, the semiconducting nanowire selected from the group consisting of Cd, CdS, CdSe, CdTe, Si, ZnO and combinations thereof;
the nanoparticle comprises an Au nanoparticle; and
the molecular spring comprises poly(ethylene glycol) (PEG) and derivatives thereof.

6. The dynamic nanoparticle structure of claim 5 further comprising a biosensing material attached to the molecular spring and residing between the metallic nanoparticle and the semiconductor nanowire.

7. The dynamic nanoparticle structure of claim 6 wherein the biosensing material is selected from the group consisting of enzymes, antibodies, nucleic acid fragments, and proteins.

8. The dynamic nanoparticle structure of claim 7 wherein the structure is water soluble.

9. A sensor comprising the dynamic nanoparticle structure of claim 7.

10. A chip comprising the sensor of claim 9.

11. The sensor of claim 9 wherein the sensor does not require a substrate.

12. The dynamic nanoparticle structure of claim 7 wherein the molecular spring is capable of reversibly expanding and contracting in length.

13. The dynamic nanoparticle structure of claim 12 wherein the molecular spring is capable of reversibly expanding and contracting in length in response to changes in environmental conditions.

14. The dynamic nanoparticle structure of claim 13 wherein changes in environmental conditions are selected from changes in pH, changes in solvent gradient and changes in temperature.

15. A dynamic nanoparticle structure comprising:
a first nanoparticle;
a second nanoparticle; and
a molecular spring, and wherein:
the first nanoparticle is connected to the second nanoparticle by the molecular spring;
the first nanoparticle comprises a metallic nanoparticle;
the second nanoparticle comprises a semiconducting nanoparticle;
the metallic nanoparticle has at least one plasmon transition state; and
the semiconducting nanoparticle has at least one exciton transition state, and wherein the metallic nanoparticle and the semiconductor nanoparticle are selected such that the at least one plasmon transition state of the metallic nanoparticle and the at least one exciton transition state of the semiconducting particle are sufficiently close in energy to resonate and couple upon excitation of the dynamic nanoparticle structure.

16. The sensor of claim 9 wherein the luminescence emission of the sensor changes in response to a change in environmental conditions.

17. The sensor of claim 16 wherein the change in the luminescence emission is selected from the group consisting of a shift in the wavelength of emission, a change in the intensity of emission, and mixtures thereof.

18. The sensor of claim 16 wherein the change in environmental conditions are selected from the group consisting of a change in pH, a change in solvent gradient, a change in temperature, and mixtures thereof.

19. The sensor of claim 17 wherein the change in environmental conditions are selected from the group consisting of a change in pH, a change in solvent gradient, a change in temperature, and mixtures thereof.

* * * * *